United States Patent

Blythin

[11] 4,272,535
[45] Jun. 9, 1981

[54] 2,4-[1H,3H,5H]-(1)-BENZOPYRANO-[2,3-d]-PYRIMIDINEDIONES AND THEIR USE AS ANTI-ALLERGY AGENTS

[75] Inventor: David J. Blythin, Caldwell, N.J.

[73] Assignee: Schering Corporation, Kenilworth, N.J.

[21] Appl. No.: 61,559

[22] Filed: Jul. 27, 1979

Related U.S. Application Data

[63] Continuation-in-part of Ser. No. 929,598, Jul. 31, 1978, abandoned.

[51] Int. Cl.³ .................. A61K 31/505; C07D 491/052
[52] U.S. Cl. .......................... 424/248.54; 424/251; 544/115; 544/250; 544/302; 560/82
[58] Field of Search ................... 424/251, 248.54; 544/250, 115

[56] References Cited

U.S. PATENT DOCUMENTS

| | | | |
|---|---|---|---|
| 3,577,420 | 5/1971 | Hess et al. | 544/250 |
| 4,013,646 | 3/1977 | Hardtmann | 424/251 X |
| 4,052,398 | 10/1977 | Kast et al. | 544/230 |

OTHER PUBLICATIONS

Schulte, et al., Arch. Pharm. Ber. Deut. Pharm. Ges. (1972), 305(5), 354–359.
Posner, Organic Reactions, vol. 19, John Wiley & Sons, (1972) pp. 3–4, 78–87.

Primary Examiner—Anton H. Sutto
Assistant Examiner—Diana G. Rivers
Attorney, Agent, or Firm—Paul H. Ginsburg

[57] ABSTRACT

Novel 2,4-(1H,3H,5H)-(1)benzopyrano-(2,3-d)-pyrimidinediones of the formula

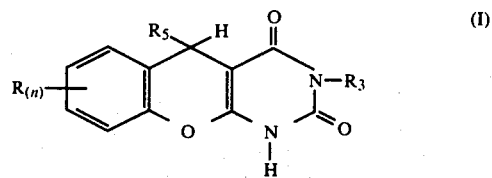

and their pharmaceutically acceptable salts are useful in the treatment of such diseases as asthma, allergic rhinitis, urticaria and ulcerative colitis.

22 Claims, No Drawings

2,4-[1H,3H,5H]-(1)-BENZOPYRANO-[2,3-D]-PYRIMIDINEDIONES AND THEIR USE AS ANTI-ALLERGY AGENTS

This application is a continuation-in-part of U.S. Ser. No. 929,598 filed July 31, 1978, now abandoned.

This invention relates to novel 2,4-(1H,3H,5H)-(1)-benzopyrano-(2,3-d)-pyrimidinediones and the pharmaceutically acceptable salts thereof, to compositions containing them, to the processes for making such compounds and compositions, and to the use of the compounds as anti-allergy agents in the treatment of such disease states as asthma, allergic rhinitis, urticaria and ulcerative colitis.

The novel compounds of this invention are of the formula

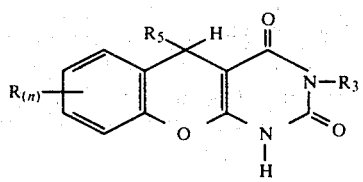

wherein each of $R_3$ and $R_5$ represents hydrogen or loweralkyl, n is an integer from one to four and R represents hydrogen, loweralkyl, lowercycloalkyl, lowercycloalkylloweralkyl, acyloxyloweralkyl, hydroxyloweralkyl, loweralkoxyloweralkyl, nitro, halogeno, haloloeralkyl, hydroxy, loweralkoxy, acylaminoloweralkyl, aminoloweralkyl, mono- or diloweralkylaminoloweralkyl, alkanoyloxy, carboxy, loweralkoxycarbonyl, acyl, formyl, cyano or a carboxamido moiety of the structure

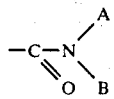

wherein A is straight or branched chain alkyl with up to 12 carbon atoms, lowercycloalkyl, lowercycloalkylloweralkyl, loweralkyloweralkyl, hydroxyloweralkyl, fluoroloweralkyl, loweralkenyl, loweralkylthioloweralkyl, loweralkylsulfoxyloweralkyl, loweralkylsulfonylloweralkyl, thiazolyl, oxazolyl, thiadiazolyl, methylthiadiazolyl, furyl, pyrazolyl, tetrazolyl, methyltetrazolyl, hydroxypyrimidinyl, phenyl, pyrimidinyl-dione, or the grouping

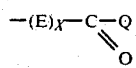

wherein E is a straight or branched chain or cyclic loweralkylene, X is zero or one and Q is hydroxy, loweralkyloxy, amino or mono- or diloeralkylamino; or the grouping —E—$R_8$, wherein E is as defined above and is optionally substituted by hydroxy and/or phenyl, $R_8$ is phenyl, thiazolyl, oxazolyl, thiadiazolyl, methylthiadiazolyl, tetrazolyl, methyltetrazolyl, furyl, pyridyl, methylpyridyl or piperidinyl; and B is hydrogen, loweralkyl, lowercycloalkyl, lowercycloalkylloweralkyl, or loweralkenyl; or A and B, when taken together with the nitrogen atom to which they are attached, represent imidazolyl, morpholinyl, pyrrolidinyl, piperidinyl or piperazinyl said heterocyclic rings being optionally substituted by hydroxy, loweralkyl or hydroxyloweralkyl; and include the pharmaceutically acceptable salts thereof.

As employed herein, the term "halogeno" refers to fluoro, chloro, bromo and iodo. The term "lower", as it modifies radicals, such as "alkyl", "alkenyl", "alkoxy" or "cycloalkyl", defines those radicals having up to seven carbon atoms. The term "loweralkyl" includes methyl, ethyl, propyl, butyl, pentyl, hexyl and heptyl and isomers thereof, such as isopropyl, t-butyl, neopentyl, 2,3-dimethylbutyl and the like. "Lowercycloalkyl" includes cyclopropyl, cyclobutyl, cyclopentyl, cyclohexyl and cycloheptyl. The term "acyloxyloweralkyl" includes those radicals embraced by the partial structure

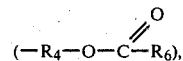

"loweralkoxyloweralkyl" includes those radicals embraced by the partial structure (—$R_4$—O—$R_1$), "haloloweralkyl" includes mono-, di- and trihalogenated lower alkyl radicals of which —$CF_3$, —$CHF_2$, —$CH_2F$, —$CHCl_2$ and $CH_2CF_3$ are preferred, "acylaminoloweralkyl" includes those radicals embraced by the partial structure

and "alkanoyloxy" includes those radicals embraced by the partial structure

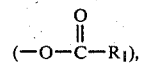

of which acetoxy is preferred, "acyl" includes those radicals embraced by the partial structure

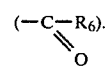

In the above partial structures $R_4$ is loweralkylene, $R_6$ is a straight or branched chain alkyl radical with up to 12 carbon atoms and $R_1$ is loweralkyl.

In a preferred group of compounds of formula I, n is one or two and the R substituent is located at the 7- and/or 8-position. At least one substituent in a multisubstituted compound is preferably in 7- or 8-position.

It is also preferred that both $R_3$ and $R_5$ represent hydrogen although, still within the preferred scope, one of $R_3$ and $R_5$ may represent methyl. Preferred R-substituents are halogen, carboxy, loweralkoxycarbonyl, acylaminoloweralkyl, acyloxyloweralkyl and the carboxamido moiety, as it is defined above, of which loweralkoxycarbonyl, acyloxyloweralkyl and the carboxamido moiety are most preferred. Within the definition of the carboxamido moiety A is preferably straight or branched chain alkyl with up to 12 carbon atoms, hydroxyloweralkyl, tetrazolyl or the grouping —E—$R_8$, wherein E is straight chain alkylene with up to three carbon atoms and is optionally substituted by hydroxy, and $R_8$ is phenyl, tetrazolyl or pyridyl; and B is hydrogen or loweralkyl. A particularly preferred carboxamido moiety is one wherein A is tetrazolyl or the grouping —E—R$_8$ with E being methylene or ethylene and R$_8$ being phenyl or pyridyl, and B is hydrogen, said moiety being located in position 7 of the molecule.

Particularly preferred compounds are 7-(5-tetrazolylaminocarbonyl)-2,4-(1H,3H,5H)-(1)-benzopyrano-(2,3-d)-pyrimidinedione and 7-(2-[2-pyridyl]ethylaminocarbonyl)-2,4-(1H,3H,5H)-(1)-benzopyrano-(2,3-d)-pyrimidinedione.

As the compounds are acidic in character they will form physiologically acceptable (i.e., pharmaceutically acceptable) metal or amine cation salts. Illustrative examples of such metals are the alkali metal, i.e., lithium, sodium and potassium, and the alkaline earth metals, i.e., magnesium and calcium. Other metals, i.e., aluminum, zinc and iron are also within the scope of this invention. Illustrative of the amines are those derived from primary, secondary or tertiary amines. Examples of suitable amines are methylamine, dimethylamine, triethylamine, ethylamine, dibutylamine, triisopropylamine, N-methylhexylamine, decylamine, dodecylamine, alllamine, crotylamine, cyclopentylamine, dicyclohexylamine, benzylamine, dibenzylamine, α-phenylethylamine, β-phenylethylamine, ethylenediamine, diethylenetriamine and like aliphatic, cycloaliphatic and aralaphatic amines containing up to and including about 18 carbon atoms, as well as heterocyclic amines, i.e., piperidine, morpholin, pyrrolidine, piperazine and lower alkyl derivatives thereof, i.e., 1-methyl piperidine, 4-ethylmorpholine, 1-isopropylpyrrolidine, 2-methylpyrrolidine, 1,4-dimethylpiperazine, 2-methylpiperidine, 1,4-dimethylpiperazine, 2-methylpiperidine and the like, as well as amines containing water solubilizing or hydrophilic groups, i.e., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris (hydroxymethyl) aminomethane, N-phenylethanolamine, N-(p-tetramylphenyl) diethanolamine, galactamine, N-methylglucamine, N-methylglucosamine and the like.

The compounds of formula I may be prepared by applying one of the following steps A to E (A) for the preparation of compounds of formula I, wherein R$_5$ is hydrogen; reducing a compound of the formula

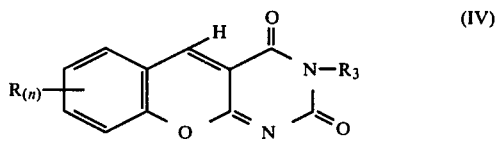

(IV)

wherein R, n and R$_3$ are as defined above; with the proviso that when R is an electron-withdrawing radical then R$_3$ is hydrogen; or (B) for the preparation of compounds of formula I, wherein R$_3$ is hydrogen and R and R$_5$ are delimited as specified in the provisos hereinbelow; cyclizing a compound of the formula

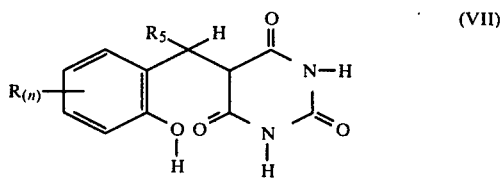

(VII)

wherein R is as defined above with the proviso that it is not acyloxyloweralkyl or alkanoyloxy; and n and R$_5$ are as defined above with the proviso that R$_5$ must be hydrogen when R is carboxy, acyl, formyl or haloloweralkyl; and wherein the hydroxy group in position 2 of the phenyl moiety may be protected; or (C) for the preparation of compounds of formula I, wherein R and n are as defined above, and R$_3$ and R$_5$ are both hydrogen, reacting a compound of the formula

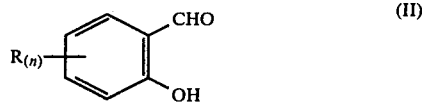

(II)

wherein R and n are as defined above, with barbituric acid in an alcoholic solvent and in the presence of a sulfonic acid; or (D) for the preparation of compounds of formula I, wherein R and n are as defined above, with the same proviso for substituent R as in process step (B), and R$_3$ and R$_5$ are both hydrogen; reacting a compound of the formula

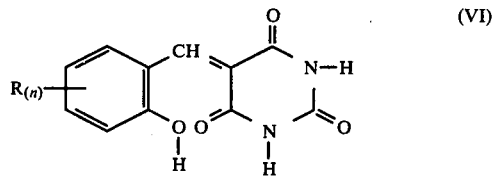

(VI)

in an alcoholic solvent and in the presence of a sulfonic acid;

(E) for the preparation of compounds of formula I, wherein R$_5$ is loweralkyl; reacting a compound of the formula

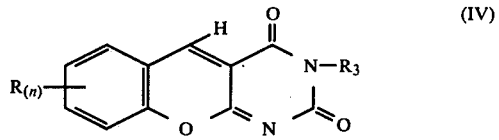

(IV)

with R$_5$'MgHal in the presence of cuprous salt, wherein R, n and R$_3$ are as defined above, R$_5$' is loweralkyl, and Hal is chlorine, bromine, or iodine; any of these steps (A) to (E) being followed by one or more of facultative finishing steps (i) to (xv) to convert a compound of formula I into another compound of formula I:

(i) esterification of the carboxyl group representing substituent R;

(ii) de-esterification of a loweralkoxycarbonyl group representing substituent R;

(iii) trans-esterification of a loweralkoxycarbonyl group representing substituent R;

(iv) acylation of any hydroxy group in/or representing substituent R;

(v) de-acylation of acyloxyloweralkyl, alkanoyloxy or acylaminoloweralkyl, representing substituent R;

(vi) reduction of an acyl group representing substituent R;

(vii) etherification of any hydroxyl group in/or representing substituent R;

(viii) hydrolysing, alcoholysing or reducing the cyano group representing substituent R;

(ix) oxydation of a hydroxymethyl group representing substituent R;
(x) acylation of an amino group in substituent R and, if desired, in situ or subsequently reducing the amide so obtained;
(xi) replacement of hydroxy by halogen in hydroxyloweralkyl representing substituent R;
(xii) amidation of the carboxyl group representing substituent R to obtain the carboxamido moiety as defined above;
(xiii) trans-amidation of a carboxamido moiety representing substituent R;
(xiv) de-amidation of a carboxamido moiety representing substituent R;
(xv) preparing a pharmaceutically acceptable salt of any of the compounds so obtained.

In step (A) reduction of a compound of formula IV is effected by standard reduction techniques, preferably by using excess molar quantities of sodium borohydride in an alcoholic medium. The reduction is preferably effected at room temperature over a period of several days or at least until a yellow-orange coloration is discharged. Excess sodium borohydride is carefully decomposed by the addition of water and acid. If substituent R is susceptible to chemical modifications in the presence of sodium borohydride (e.g., formyl, acyl) then neutral conditions such as provided for by sodium cyanoborohydride are advantageously employed.

Alternatively, the desired compound of formula I can also be obtained from a compound of formula IV by heating the latter in the presence of a sulfonic acid, such as p-toluenesulfonic acid or methanesulfonic acid, in an alcoholic solvent, such as propanol or butanol. This process is inventive as the use of a sulfonic acid alcohol as a reducing system has not been described heretofore.

The following reaction scheme illustrates the reaction thereby showing the reaction from starting materials well known in the art:

gen, loweralkyl, lowercycloalkyl, lowercycloalkylloweralkyl, acyloxyloweralkyl, hydroxyloweralkyl, monohalogeno, loweralkoxy, acylaminoloweralkyl, aminoloweralkyl, mono- and diloweralkylaminoloweralkyl, alkanoyloxy and loweralkoxyloweralkyl. Electron-withdrawing groups within the scope of R are such groups as loweralkoxycarbonyl, dihalogeno, nitro, carboxy, carboxamido, formyl, acyl, cyano, trifluoromethyl, difluoromethyl and the like.

In those instances wherein the initial reaction is to condense the substituted salicylaldehyde (IIa) with the cyanoacetylurethane there is produced an appropriately Y-substituted 2,4-(3H)-(1)-benzopyrano-(2,3-d)-pyrimidinedione intermediate (IV) which is isolated and may then be converted to a final product (I). The condensation is preferably effected in an alcoholic solvent, preferably ethanol, and catalytic quantities of a secondary base, preferably morpholine although other equivalently functioning bases may be employed. Generally, equimolar quantities of the reactants may be employed although in practice it is preferred to have a slight excess of the cyanoacetyl urethane. The reaction is preferably effected at reflux temperature and is continued for times up to eight hours after a yellow-orange precipitate starts to form.

In those instances wherein the initial reaction involves the condensation of an appropriately substituted salicylaldehyde (IIb) with barbituric acid (V), there is produced a 5-[(2-hydroxy)-$Z_{(n)}$-phenylmethylene]-2,4,6-(1H-3H)-pyrimidinetrione (VIb) intermediate. This condensation reaction is effected by heating an admixture of reactants at elevated temperatures (60°–100° C.), preferably 90° C., in an inert organic solvent (preferably aqueous dioxan) for about 0.5–12 hours. The intermediate (VIb) is then converted into intermediate (IV) by standard dehydration techniques such as employing an acid anhydride, e.g., acetic anhydride, at reflux temperature.

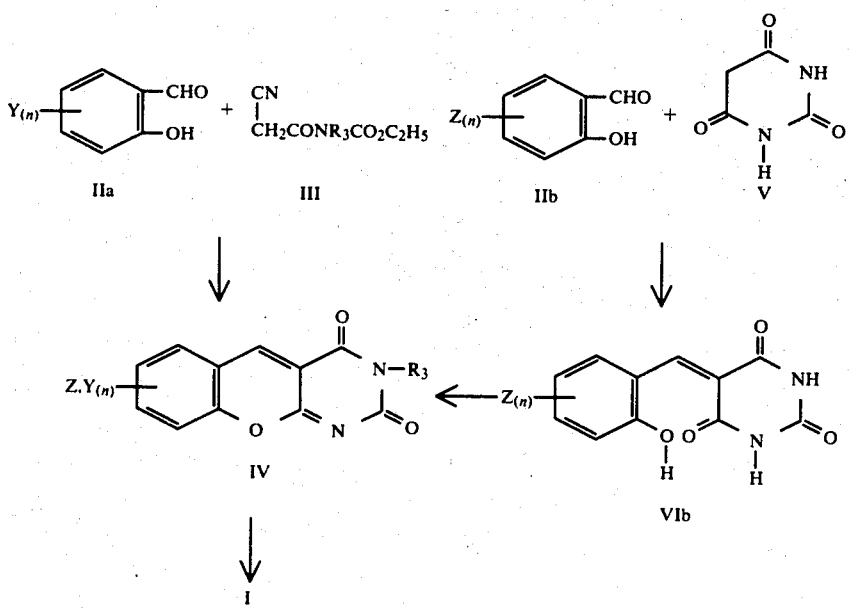

wherein n and $R_3$ are as previously defined, Y is an electron-donating radical within the scope of R and Z is an electron-withdrawing radical within the scope of R with R being as previously defined. Electron-donating groups within the scope of R are such groups as hydro- In the above reaction scheme, specifically in compound (IV), the phenyl substituent $R_{(n)}$ is shown as $Z;Y_{(n)}$. As per the definitions of R, Z and Y it is apparent that R and (Z,Y) are synonymous. The proviso in process step (A) is also apparent from the above reaction scheme, as $R_3$ must be hydrogen if (IV) is obtained from (IIb) and (V) via (VIb).

In process step (B) cyclisation of a compound (VII) is effected by standard dehydration techniques such as by heating the compound (VII) in the presence of polyphosphoric acid or phosphorous oxychloride, or by heating the compound (VII) with sulfonic acids (preferably methanesulfonic acid) in the presence of such catalysts as phosphorous pentoxide or the like.

Alternatively, a mixture of a compound (VII) and a pyridine hydrohalide is heated to melting.

The following reaction scheme illustrates the reaction thereby showing the reaction from starting materials well known in the art or described hereinabove:

that it is not acyloxyloweralkyl, haloloweralkyl, alkanoyloxy, carboxy, acyl or formyl.

In the above reaction scheme the substituted salicylaldehyde IIc, the 2-hydroxy group of which is protected, is condensed with diethyl malonate according to methods known in the art to yield the benzylidene malonate (VIII). Depending on whether a final compound (I) is desired wherein $R_5$ is hydrogen or loweralkyl ($R_5'$), the compound of formula (VIII) is either first reduced to the benzyl malonate which compound is then reacted with urea according to a method known in the art (J. A. Vida, et al, *J. Med. Chem.*, 17, 732 (1974)) to yield a pyrimidinetrione (VIIc) ($R_5$=H), or the compound of formula (VIII) is reacted with the Grignard reagent $R_5'$MgHal in the presence of a cuprous salt, such as cuproius iodide, to introduce the desired $R_5'$

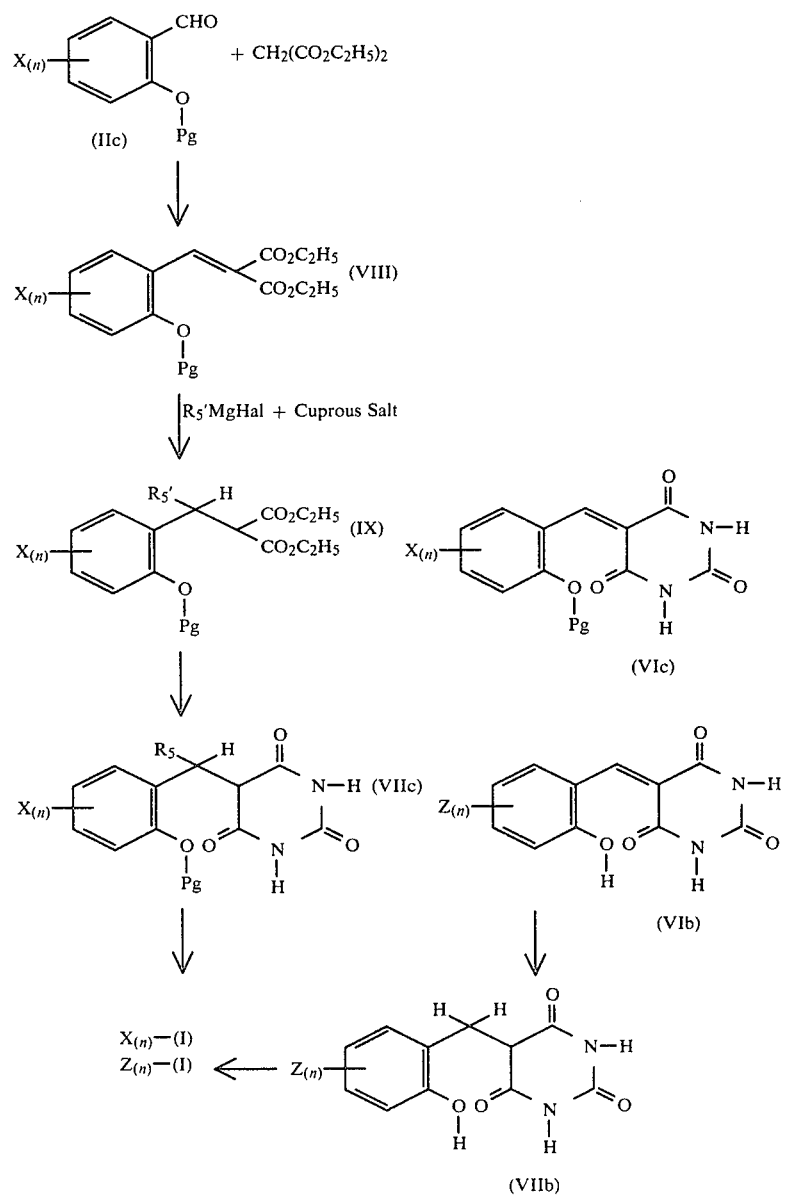

wherein Z, n and $R_5$ are as previously defined, $R_5'$ is loweralkyl, Hal is chlorine, bromine or iodine, Pg is a hydroxy-protective group, such as benzyl, and X is the same as R being previously defined with the proviso group and to yield compound (IX) which is then reacted with urea as described above for the foregoing benzyl malonate.

Alternatively, a compound of formula (VIb) as described in a previous reaction scheme is reduced to a pyrimidinetrione (VIIb). This reduction as well as the reduction of compound (VIc) is effected according to such known methods as using sodiumborohydride or, if substituent Z is susceptible to chemical modification, sodiumcyanoborohydride providing neutral conditions.

It is readily apparent from the above reaction scheme and the definitions of R, X and Z that R, if it is not acyloxylower alkyl or alkanoyloxy, corresponds to the scope of X and Z when taken together. Thus, compounds (VIIb) and (VIIc), if taken together, are also identified herein as compounds (VII) having a R-substituent (with a proviso) rather than an X- or Z-substituent. The proviso relating to $R_5$ in process step (B) is also apparent from the definition of substituent X and the above reaction scheme, as $R_5$ can only be loweralkyl in that case when the route from (IIc) via (IX) is followed.

The reaction in process step (C) is inventive as such as heretofore it was completely unexpected that a substituted salicylaldehyde (II), upon reaction with barbituric acid in an alcoholic solvent, such as n-propanol, n-butanol or iso-propanol, and in the presence of a sulfonic acid, such as methanesulfonic acid or p-toluenesulfonic acid, yields compounds of formula (I) in good yields. Apparently, intermediates are formed in situ during this reaction which have the structure of compounds (VIb) and (VIc) (the latter without the hydroxy protective group $P_g$) and also the structure of compounds (IV). If these compounds are prepared as described in connection with the two reaction schemes above and are subjected to the reaction conditions of process step (C), compounds of formula (I) are also obtained. Accordingly, in process step (D) the same reaction conditions ought to be applied as described in relation to process step (C) and, as it is true for process step (C), also process step (D) is inventive as such. The compounds of formula (VI) may be obtained for compounds (VIb) and (VIc).

Process step (E) represents a method for obtaining compounds of formula (I), wherein $R_5$ is loweralkyl, and thus, for example, is a convenient route for preparing compounds wherein both $R_3$ and $R_5$ are loweralkyl. The reaction represents the addition of a Grignard reagent, such as $CH_3MgI$, to a double bond in the presence of a cuprous salt, such as cuprous iodide. The preparation of compounds of formula (IV) is described in detail in connection with the above reaction schemes.

All of the facultative finishing steps represent chemical reactions well known in the art such as esterification, amidation, acylation and the like. They are useful when particular R-substituted compounds must be prepared and the correspondingly substituted starting materials are not available or the use thereof would reduce the overall yield.

The following examples illustrate the invention.

EXAMPLE I

7-HYDROXYMETHYL-2,4-(1H,3H,5H)-(1)-BENZOPYRANO-(2,3-d)-PYRIMIDINEDIONE

A(1)
7-Hydroxymethyl-2,4-(3H)-(1)-Benzopyrano-(2,3-d)-Pyrimidinedione:

To a warmed and stirred solution containing 5-hydroxy methylsalicylaldehyde (46 g) and N-cyanoacetylurethane (48 g) in absolute ethanol, add morpholine (0.5 ml) and reflux the resulting solution for 4 hours. After cooling, filter, ethanol wash and dry the product to yield 7-hydroxymethyl-2,4-(3H)-(1)-benzopyrano-(2,3-d)-pyrimidinedione.

In a similar manner, by replacing the 5-hydroxymethyl salicylaldehyde with equivalent quantities of the appropriately substituted salicylaldehyde, and by substantially following the procedure of this example, there are produced the following compounds:

2,4-(3H)-(1)-benzopyrano-(2,3-d)-pyrimidinedione,
7-methyl-2,4-(3H)-(1)-benzopyrano-(2,3-d)-pyrimidinedione,
7-cyclopropyl-2,4-(3H)-(1)-benzopyrano-(2,3-d)-pyrimidinedione,
7-t-butyl-2,4-(3H)-(1)-benzopyrano-(2,3-d)-pyrimidinedione,
7,8-dimethyl-2,4-(3H)-(1)-benzopyrano-(2,3-d)-pyrimidinedione,
7,9-dihydroxymethyl-2,4-(3H)-(1)-benzopyrano-(2,3-d)-pyrimidinedione,
7-methyl-8-chloro-2,4-(3H)-(1)-benzopyrano-(2,3-d)-pyrimidinedione,
7,8-dihydroxy-2,4-(3H)-(1)-benzopyrano-(2,3-d)-pyrimidinedione,
6-chloro-2,4-(3H)-(1)-benzopyrano-(2,3-d)-pyrimidinedione,
7-bromo-2,4-(3H)-(1)-benzopyrano-(2,3-d)-pyrimidinedione,
9-ethoxy-2,4-(3H)-(1)-benzopyrano-(2,3-d)-pyrimidinedione,
7-chloro-2,4-(3H)-(1)-benzopyrano-(2,3-d)-pyrimidinedione,
7,8-dichloro-2,4-(3H)-(1)-benzopyrano-(2,3-d)-pyrimidinedione,
8-hydroxy-7-aminomethyl-2,4-(3H)-(1)-benzopyrano-(2,3-d)-pyrimidinedione,
7-dimethylaminomethyl-2,4-(3H)-(1)-benzopyrano-(2,3-d)-pyrimidinedione,
7-hydroxy-2,4-(3H)-(1)-benzopyrano-(2,3-d)-pyrimidinedione,
8-methoxy-2,4-(3H)-(1)-benzopyrano-(2,3-d)-pyrimidinedione.

Similarly, by replacing the N-cyanoacetyl urethane reactant with equivalent quantities of N-cyanoacetyl-N-methylurethane or N-cyanoacetyl-N-ethyl-urethane and by substantially following the foregoing reaction conditions, there are produced the 3-methyl analogs or 3-ethyl analogs of the foregoing enumerated compounds.

(2)
8-chloro-2,4-(3H)-(1)-benzopyrano-(2,3-d)-pyrimidinedione:

Dissolve a mixture of 4-chlorosalicylaldehyde (6 g) and N-cyanoacetylurethane (6 g) in a minimum quantity of ethanol at room temperature. Add morpholine (60 mg) and allow the resulting solution to stand at room temperature overnight. Filter and wash the solid with ethanol. This product, after drying, is heated, with stirring, at 165° C. for 2½ hours. Add ethanol to the solid, filter, wash with ethanol and then with ether. Dry the product to yield 8-chloro-2,4-(3H)-(1)-benzopyrano-(2,3-d)-pyrimidinedione.

B:
7-Hydroxymethyl-2,4-(1H,3H,5H)-(1)-Benzopyrano-(2,3-d)-Pyrimidinedione

To a suspension of 7-hydroxymethyl-2,4-(3H)-(1)-benzopyrano-(2,3-d)-pyrimidinedione (18.8 g) in isopropanol (600 ml) add, in portions during one hour, sodium borohydride (12 g). Stir the mixture for two days at room temperature. Carefully add water to decompose the excess borohydride and then add 5.5 N hydrochloric acid until the mixture is acidic. Filter, wash consecutively with water, isopropanol, and ether, and dry the product to yield 7-hydroxymethyl-2,4-(1H,3H,5H)-(1)-benzopyrano-(2,3-d)-pyrimidinedione, dec. 308°–309,5° C.

In a similar manner, by replacing the (3H)-(1)-benzopyrano-(2,3-d)-pyrimidinedione reactants of this part with equivalent quantities of those compounds prepared by the technique of part A of this example, and by substantially following the foregoing teachings, there are produced.

2,4-(1H,3H,5H)-(1)-benzopyrano-(2,3-d)-pyrimidinedione, dec. 310° C.,
7-methyl-2,4-(1H,3H,5H)-(1)-benzopyrano-(2,3-d)-pyrimidinedione,
7-cyclopropyl-2,4-(1H,3H,5H)-(1)-benzopyrano-(2,3-d)-pyrimidinedione,
7-t-butyl-2,4-(1H,3H,5H)-(1)-benzopyrano-(2,3-d)-pyrimidinedione,
7,8-dimethyl-2,4-(1H,3H,5H)-(1)-benzopyrano-(2,3-d)-pyrimidinedione, m.p. >360° C.,
7,9-dihydroxymethyl-2,4-(1H,3H,5H)-(1)-benzopyrano-(2,3-d)-pyrimidinedione,
7-methyl-8-chloro-2,4-(1H,3H,5H)-(1)-benzopyrano-(2,3-d)-pyrimidinedione,
8-hydroxy-2,4-(1H,3H,5H)-(1)-benzopyrano-(2,3-d)-pyrimidinedione, chars 330° C.,
7,8-dihydroxy-2,4-(1H,3H,5H)-(1)-benzopyrano-(2,3-d)-pyrimidinedione,
6-chloro-2,4-(1H,3H,5H)-(1)-benzopyrano-(2,3-d)-pyrimidinedione,
7-bromo-2,4-(1H,3H,5H)-(1)-benzopyrano-(2,3-d)-pyrimidinedione,
9-ethoxy-2,4-(1H,3H,5H)-(1)-benzopyrano-(2,3-d)-pyrimidinedione,
7-chloro-2,4-(1H,3H,5H)-(1)-benzopyrano-(2,3-d)-pyrimidinedione,
7-bromo-8-chloro-2,4-(1H,3H,5H)-(1)-benzopyrano-(2,3-d)-pyrimidinedione, chars 330° C.,
7,8-dichloro-2,4-(1H,3H,5H)-(1)-benzopyrano-(2,3-d)-pyrimidinedione,
8-hydroxy-7-aminomethyl-2,4-(1H,3H,5H)-(1)-benzopyrano-(2,3-d)-pyrimidinedione,
7-acetoxymethyl-2,4-(1H,3H,5H)-(1)-benzopyrano-(2,3-d)-pyrimidinedione, chars 320° C.,
7-dodecanoyloxymethyl-2,4-(1H,3H,5H)-(1)-benzopyrano-(2,3-d)-pyrimidinedione, m.p. 229°–232° C.,
7-dimethylaminomethyl-2,4-(1H,3H,5H)-(1)-benzopyrano-(2,3-d)-pyrimidinedione,
8-acetoxy-2,4-(1H,3H,5H)-(1)-benzopyrano-(2,3-d)-pyrimidinedione, chars 295° C.,
7-hydroxy-2,4-(1H,3H,5H)-(1)-benzopyrano-(2,3-d)-pyrimidinedione,
7-(isobutyrylaminomethyl)-8-methoxy-2,4-(1H,3H,5H)-(1)-benzopyrano-(2,3-d)-pyrimidinedione,
7-(isopropylaminomethyl)-2,4-(1H,3H,5H)-(1)-benzopyrano-(2,3-d)-pyrimidinedione,
8-methoxy-2,4-(1H,3H,5H)-(1)-benzopyrano-(2,3-d)-pyrimidinedione, dec. 305° C.,
6,8-dimethoxy-2,4-(1H,3H,5H)-(1)-benzopyrano-(2,3-d)-pyrimidinedione,
and the 3-methyl and 3-ethyl homologs of the foregoing, such as 3-ethyl-7-hydroxymethyl-2,4-(1H,3H,5H)-(1)-benzopyrano-(2,3-d)-pyrimidinedione, m.p. 285° C.

EXAMPLE II

7-METHOXYCARBONYL-2,4-(1H,3H,5H)-(1)-BENZOPYRANO-(2,3-d)-PYRIMIDINEDIONE

5-[2'-Hydroxy-5'-Methoxycarbonyl)-Phenyl-Methylene]-2,4,6-(1H,3H)-Pyrimidinetrione On a steam bath, heat a solution of methyl 3-formyl-4-hydroxybenzoate (6 g) and barbituric acid (5 g) in a minimum volume of aqueous dioxan for one hour and allow the mixture to stand at room temperature overnight. Add water, evaporate off the dioxan and filter the precipitated product. Wash the product with water and isopropanol and dry in vacuo.

(B)

5-(2'-Hydroxy-5'-Methoxycarbonyl)-Benzyl-2,4,6-(1H,3H,5H)-Pyrimidinetrione

Suspend 5-[2'-hydroxy-5'-methoxycarbonyl)-phenyl-methylene]-2,4,6-(1H,3H)-pyrimidinetrione (2.3 g) in isopropanol (100 ml) with stirring and in small portions (0.2 g) add sodium borohydride (at intervals of ½ hour) until the color of the solid does not change further. After a further one hour, cautiously add water and then acidify the mixture with 5.5 N hydrochloric acid. Add more water (150 ml), evaporate off the isopropanol, and filter, water-wash and dry the resulting product.

(C)

7-Methoxycarbonyl-2,4-(1H,3H,5H)-(1)-Benzopyrano-(2,3-d)-Pyrimidinedione

To a stirred solution of phosphorous pentoxide (70 g) in methanesulfonic acid (600 g) at 80° C. add 5-(2'-hydroxy-5'-methoxycarbonyl)-benzyl-2,4,6-(1H,3H,5H)-pyrimidinetrione (25.0 g) and keep the resulting solution at 80° C. for four hours. Cool and pour the solution over ice and water. Filter and wash the precipitate with water and then with ethanol. Dry the product to yield 7-methoxycarbonyl-2,4-(1H,3H,5H)-(1)-benzopyrano-(2,3-d)-pyrimidinedione, dec. 320° C.

Similarly, by substituting the 3-formyl-4-hydroxybenzoate reactant of this example with equivalent quantities of the appropriate R(n)-substituted-4-hydroxybenzoates and by substantially following the procedures of Parts A, B and C of this example, there are produced the following compounds:

7-carboethoxy-2,4-(1H,3H,5H)-(1)-benzopyrano-(2,3-d)-pyrimidinedione,
6-carbomethoxy-2,4-(1H,3H,5H)-(1)-benzopyrano-(2,3-d)-pyrimidinedione,
8-carbomethoxy-2,4-(1H,3H,5H)-(1)-benzopyrano-(2,3-d)-pyrimidinedione,
9-carbomethoxy-2,4-(1H,3H,5H)-(1)-benzopyrano-(2,3-d)-pyrimidinedione,
7,8-dicarbomethoxy-2,4-(1H,3H,5H)-(1)-benzopyrano-(2,3-d)-pyrimidinedione,
7-acetyl-2,4-(1H,3H,5H)-(1)-benzopyrano-(2,3-d)-pyrimidinedione,
7,8-diacetyl-2,4-(1H,3H,5H)-(1)-benzopyrano-(2,3-d)-pyrimidinedione,
7-butyryl-2,4-(1H,3H,5H)-(1)-benzopyrano-(2,3-d)-pyrimidinedione,
7-cyclobutylcarbonyl-2,4-(1H,3H,5H)-(1)-benzopyrano-(2,3-d)-pyrimidinedione,
7,8-dichloro-2,4-(1H,3H,5H)-(1)-benzopyrano-(2,3-d)-pyrimidinedione, 7-chloro-2,4-(1H,3H,5H)-(1)-benzopyrano-(2,3-d)-pyrimidinedione,
8-bromo-2,4-(1H,3H,5H)-(1)-benzopyrano-(2,3-d)-pyrimidinedione,
7-trifluoromethyl-2,4-(1H,3H,5H)-(1)-benzopyrano-(2,3-d)-pyrimidinedione,
7-trifluoromethyl-8-chloro-2,4-(1H,3H,5H)-(1)-benzopyrano-(2,3-d)-pyrimidinedione,
7-cyano-2,4-(1H,3H,5H)-(1)-benzopyrano-(2,3-d)-pyrimidinedione,
7-cyano-8-chloro-2,4-(1H,3H,5H)-(1)-benzopyrano-(2,3-d)-pyrimidinedione.

EXAMPLE III

7-NITRO-2,4-(1H,3H,5H)-(1)-BENZOPYRANO-(2,3-d)-PYRIMIDINEDIONE

Reflux a mixture containing 5-[2'-hydroxy-5'-nitro)-phenylmethylene]-2,4,6-(1H,3H)-pyrimidinetrione (56 g) and acetic anhydride (1000 ml) for four hours. Filter off and wash the solid product with ether to yield 7-nitro-2,4-(3H)-(1)-benzopyrano-(2,3-d)-pyrimidinedione which, by following the procedure of Example I, Part B, yields the desired 7-nitro-2,4-(1H,3H,5H)-(1)-benzopyrano-(2,3-d)-pyrimidinedione.

EXAMPLE IV

7-BROMO-5-METHYL-2,4-(1H,3H,5H)-(1)-BENZOPYRANO-(2,3-d)-PYRIMIDINEDIONE

α-(2-Benzyloxy-5-Bromo) Phenethyl Malonate

To a cooled (−30° C.) mixture of diethyl-2-benzyloxy-5-bromobenzylidene malonate (30 g) in ether (300 ml) add cuprous iodide (3.8 g) followed by a freshly prepared methyl magnesium iodide solution (from 5.1 g of magnesium and 31 g of methyl iodide in about 250 ml of ether). After the addition allow the reaction mixture to stand at room temperature for 4 hours, add a cold aqueous ammonium chloride solution and acidify with 5 N HCl. Separate the organic layer and extract the aqueous layer with ethyl acetate which is combined with the separated organic layer. Dry the combined material (over Na$_2$SO$_4$), evaporate off the solvents to produce an oil which solidifies after a time.

(B) 5-[α-(2-Benzyloxy-5-Bromo)phenyl] Ethyl Barbituric Acid

α-(2-benzyloxy-5-bromo)phenethyl malonate (22.5 g) is treated with urea and sodium in ethanol according to the published procedure of J. A. Vida, et al, *J. Med. Chem.*, 17, 732 (1974) to yield 5-[α-(2-benzyloxy-5-bromo)phenyl]ethyl barbituric acid.

(C)
7-Bromo-5-Methyl-2,4-(1H,3H,5H)-(1)-Benzopyrano-(2,3-d)-Pyrimidinedione

In an atmosphere of nitrogen and with constant stirring, heat to melting a mixture of 5-[α-(2-benzyloxy-5-bromo)phenyl]ethyl barbituric acid (5 g) and pyridine hydrochloride (15 g). Heat the resulting solution at 150° C. for 6 hours and after cooling, add water, filter and wash the resulting white solid with water, ethanol and then ether. Dry the product to yield 7-bromo-5-methyl-2,4-(1H,3H,5H)-(1)-benzopyrano-(2,3-d)-pyrimidinedione. Also produced by this method are:
5-methyl-2,4-(1H,3H,5H)-(1)-benzopyrano-(2,3-d)-pyrimidinedione, dec. 262° C.,
5,7-dimethyl-2,4-(1H,3H,5H)-(1)-benzopyrano-(2,3-d)-pyrimidinedione,
5-methyl-7-t-butyl-2,4-(1H,3H,5H)-(1)-benzopyrano-(2,3-d)-pyrimidinedione,
5,7,8-trimethyl-2,4-(1H,3H,5H)-(1)-benzopyrano-(2,3-d)-pyrimidinedione,
5,7-dimethyl-8-chloro-2,4-(1H,3H,5H)-(1)-benzopyrano-(2,3-d)-pyrimidinedione,
5-methyl-6-chloro-2,4-(1H,3H,5H)-(1)-benzopyrano-(2,3-d)-pyrimidinedione,
5-methyl-9-ethoxy-2,4-(1H,3H,5H)-(1)-benzopyrano-(2,3-d)-pyrimidinedione,
5-methyl-7-chloro-2,4-(1H,3H,5H)-(1)-benzopyrano-(2,3-d)-pyrimidinedione,
5-methyl-7,8-dichloro-2,4-(1H,3H,5H)-(1)-benzopyrano-(2,3-d)-pyrimidinedione,

EXAMPLE V

7-CYANO-2,4-(1H,3H,5H)-(1)-BENZOPYRANO-(2,3-d)-PYRIMIDINEDIONE

To n-butanol (40 ml) add 5-cyanosalicylaldehyde (3 g) barbituric acid (2.8 g) and methanesulfonic acid (4 ml). Stir and heat to reflux for two hours, cool, filter and wash the solid with isopropanol and ether to yield 7-cyano-2,4-(1H,3H,5H)-(1)-benzopyrano-(2,3-d)-pyrimidinedione.

Also, by the technique of this example there are produced:
7-nitro-2,4-(1H,3H,5H)-(1)-benzopyrano-(2,3-d)-pyrimidinedione,
9-methoxy-2,4-(1H,3H,5H)-(1)-benzopyrano-(2,3-d)-pyrimidinedione,
7-methyl-2,4-(1H,3H,5H)-(1)-benzopyrano-(2,3-d)-pyrimidinedione,
7-n-butyl-2,4-(1H,3H,5H)-(1)-benzopyrano-(2,3-d)-pyrimidinedione,
7-t-butyl-2,4-(1H,3H,5H)-(1)-benzopyrano-(2,3-d)-pyrimidinedione,
7,8-dimethyl-2,4-(1H,3H,5H)-(1)-benzopyrano-(2,3-d)-pyrimidinedione,
7-methyl-8-chloro-2,4-(1H,3H,5H)-(1)-benzopyrano-(2,3-d)-pyrimidinedione,
6-chloro-2,4-(1H,3H,5H)-(1)-benzopyrano-(2,3-d)-pyrimidinedione,
7-bromo-2,4-(1H,3H,5H)-(1)-benzopyrano-(2,3-d)-pyrimidinedione,
9-ethoxy-2,4-(1H,3H,5H)-(1)-benzopyrano-(2,3-d)-pyrimidinedione,
7-chloro-2,4-(1H,3H,5H)-(1)-benzopyrano-(2,3-d)-pyrimidinedione,
7,8-dichloro-2,4-(1H,3H,5H)-(1)-benzopyrano-(2,3-d)-pyrimidinedione.

EXAMPLE VI

7-METHOXYCARBONYL-2,4-(1H,3H,5H)-(1)-BENZOPYRANO-(2,3-d)-PYRIMIDINEDIONE

Dissolve p-toluene sulfonic acid (2 g) in sec-butanol (50 ml). Add 5-(2'-hydroxy-5'-methoxycarbonyl)-benzylidene-2,4,6-(1H,3H)-pyrimidinetrione (1.45 g), and reflux for about 18 hours. Allow to cool, add to water, filter, wash with water, isopropanol and ether consecutively to yield 7-methoxycarbonyl-2,4-(1H,3H,5H)-(1)-benzopyrano-(2,3-d)-pyrimidinedione, dec. 320° C.

Also, by the techniques of this example, there are produced:
7-ethoxycarbonyl-2,4-(1H,3H,5H)-(1)-benzopyrano-(2,3-d)-pyrimidinedione, 7-isopropoxycarbonyl-2,4-(1H,3H,5H)-(1)-benzopyrano-(2,3-d)-pyrimidinedione,
7-cyano-2,4-(1H,3H,5H)-(1)-benzopyrano-(2,3-d)-pyrimidinedione,
7-nitro-2,4-(1H,3H,5H)-(1)-benzopyrano-(2,3-d)-pyrimidinedione.

EXAMPLE VII

9-METHOXY-2,4-(1H,3H,5H)-(1)-BENZOPYRANO-(2,3-d)-PYRIMIDINEDIONE

To a suspension of 9-methoxy-2,4-(3H)-(1)-benzopyrano-(2,3-d)-pyrimidinedione, (24.4 g) in isopropanol (100 ml) add p-toluene sulfonic acid (6 g). Reflux for 40 hours. Cool and filter. Wash with water then with isopropanol and, finally, ether to yield 9-methoxy-2,4-(1H,3H,5H)-(1)-benzopyrano-(2,3-d)-pyrimidinedione.

Also, by the technique of this example, there are produced the following compounds:

7-cyclopropyl-2,4-(1H,3H,5H)-(1)-benzopyrano-(2,3-d)-pyrimidinedione,
7-t-butyl-2,4-(1H,3H,5H)-(1)-benzopyrano-(2,3-d)-pyrimidinedione,
7,8-dimethyl-2,4-(1H,3H,5H)-(1)-benzopyrano-(2,3-d)-pyrimidinedione,
7-methyl-8-chloro-2,4-(1H,3H,5H)-(1)-benzopyrano-(2,3-d)-pyrimidinedione,
6-chloro-2,4-(1H,3H,5H)-(1)-benzopyrano-(2,3-d)-pyrimidinedione,
7-bromo-2,4-(1H,3H,5H)-(1)-benzopyrano-(2,3-d)-pyrimidinedione,
9-ethoxy-2,4-(1H,3H,5H)-(1)-benzopyrano-(2,3-d)-pyrimidinedione,
7-chloro-2,4-(1H,3H,5H)-(1)-benzopyrano-(2,3-d)-pyrimidinedione,
7,8-dichloro-2,4-(1H,3H,5H)-(1)-benzopyrano-(2,3-d)-pyrimidinedione,
8-methoxy-2,4-(1H,3H,5H)-(1)-benzopyrano-(2,3-d)-pyrimidinedione,
7,9-dibromo-2,4-(1H,3H,5H)-(1)-benzopyrano-(2,3-d)-pyrimidinedione,
8-trifluoromethyl-2,4-(1H,3H,5H)-(1)-benzopyrano-(2,3-d)-pyrimidinedione.

EXAMPLE VIII

7-CARBOXY-(1H,3H,5H)-(1)-BENZOPYRANO-(2,3-d)-PYRIMIDINEDIONE

Warm a suspension of 7-methoxycarbonyl-2,4-(1H,3H,5H)-(1)-benzopyrano-(2,3-d)-pyrimidinedione (5 g) in 1 N sodium hydroxide (25 ml) until a clear solution is formed and continue the warming for an additional ½ hour. Filter the solution and acidify the filtrate with 2 N sulfuric acid. Filter and wash the solids with water, isopropanol and then ether. Dry the washed solid to obtan 7-carboxy-2,4-(1H,3H,5H)-(1)-benzopyrano-(2,3-d)-pyrimidinedione.H$_2$O; m.p. >360° C.

Also produced by this method are:

7-carboxy-3-methyl-2,4-(1H,3H,5H)-(1)-benzopyrano-(2,3-d)-pyrimidinedione,
7-carboxy-3-ethyl-2,4-(1H,3H,5H)-(1)-benzopyrano-(2,3-d)-pyrimidinedione,
7-carboxy-5-methyl-2,4-(1H,3H,5H)-(1)-benzopyrano-(2,3-d)-pyrimidinedione,
6-carboxy-2,4-(1H,3H,5H)-(1)-benzopyrano-(2,3-d)-pyrimidinedione,
8-carboxy-2,4-(1H,3H,5H)-(1)-benzopyrano-(2,3-d)-pyrimidinedione,
9-carboxy-2,4-(1H,3H,5H)-(1)-benzopyrano-(2,3-d)-pyrimidinedione,
7,8-dicarboxy-2,4-(1H,3H,5H)-(1)-benzopyrano-(2,3-d)-pyrimidinedione.

EXAMPLE IX

7-(ISOBUTYRYLOXYMETHYL)-2,4-(1H,3H,5H)-(1)-BENZOPYRANO-(2,3-d)-PYRIMIDINEDIONE

To a cooled (below 5° C.) suspension of 7-hydroxymethyl-2,4-(1H,3H,5H)-(1)-benzopyrano-(2,3-d)-pyrimidinedione.⅓ H$_2$O (2.56 g) in dry pyridine (100 ml), add isobutyric anhydride (20 ml). Keep the mixture cold for 24 hours and stir the mixture at 20° C. for an additional two days. Pour the mixture over ice/water, filter and successively wash the solids with water, ethanol and ether. Dry the washed solids to obtain 7-(isobutyryloxymethyl)-2,4-(1H,3H,5H)-(1)-benzopyrano-(2,3-d)-pyrimidinedione, m.p. 264.5°–265° C.

Similarly, by starting with other pyridiminediones of this invention which bear one or more reactive hydroxyl groups (i.e., when R represents hydroxy or hydroxyalkyl), the foregoing esterification may be effected. Analogously, by utilizing the acid chloride or anhydride of the appropriate acid and following the techniques of this example, the following esters (of either the hydroxy or the hydroxyalkyl substituents) may be prepared: acetyl, propionyl, n-butyryl, isobutyryl, pivaloyl, t-butylacetyl, and lauroyl.

Additionally such esters are also formed from all the other compounds bearing a reactive hydroxy moiety as a substituent in the benzenoid moiety of the benzopyrano pyrimidinedione compounds.

EXAMPLE X

7-(1'-HYDROXYETHYL)-2,4-(1H,3H,5H)-(1)-BENZOPYRANO-(2,3-d)-PYRIMIDINEDIONE

To a stirred suspension of 7-acetyl-2,4-(1H,3H,5H)-(1)-benzopyrano-(2,3-d)-pyrimidinedione (0.5 g) in isopropanol (75 ml) add sodium borohydride (0.36 g) and continue stirring the resulting mixture at room temperature for 3½ hours. Carefully add water and then add a saturated solution of ammonium chloride. Acidify the mixture with 5.5 N hydrochloric acid, evaporate off the isopropanol, filter and wash the product with water and isopropanol to yield 7-(1'-hydroxyethyl)-2,4-(1H,3H,5H)-(1)-benzopyrano-(2,3-d)-pyrimidinedione, m.p. 270°–274° C.

Also, by the methodology of ths example there may be produced the following compounds:

7-(1'-hydroxypropyl)-2,4-(1H,3H,5H)-(1)-benzopyrano-(2,3-d)-pyrimidinedione,
7-(1'-hydroxybutyl)-2,4-(1H,3H,5H)-(1)-benzopyrano-(2,3-d)-pyrimidinedione.

EXAMPLE XI

7-(n-PENTYLOXYMETHYL)-2,4-(1H,3H,5H)-(1)-BENZOPYRANO-(2,3-d)-PYRIMIDINEDIONE

Reflux (136°–138° C.) a mixture of 2.5 g of 7-hydroxymethyl-2,4-(1H,3H,5H)-(1)-benzopyrano-(2,3-d)-pyrimidinedione. ⅓ H$_2$O, 3.8 g of p-toluenesulfonic acid monohydrate and 250 ml of n-pentanol until the solution becomes homogeneous. Concentrate the solution until a solid begins to appear at which time the solution is cooled, diluted with ether (250 ml), filtered, triturated, and washed with fresh ether to yield 7-(n-pentyloxymethyl)-2,4-(1H,3H,5H)-(1)-benzopyrano-(2,3-d)-pyrimidinedione. ½ H₂O.

Also by substantially following the teachings of this example (except the reactants are heated to 130°–140° C. under pressure) there are produced the following compounds:

7-n-butyloxymethyl-2,4-(1H,3H,5H)-(1)-benzopyrano-(2,3-d)-pyrimidinedione,
7-iso-butyloxymethyl-2,4-(1H,3H,5H)-(1)-benzopyrano-(2,3-d)-pyrimidinedione,
7-n-propyloxymethyl-2,4-(1H,3H,5H)-(1)-benzopyrano-(2,3-d)-pyrimidinedione,
7-iso-propyloxymethyl-2,4-(1H,3H,5H)-(1)-benzopyrano-(2,3-d)-pyrimidinedione,
7-ethoxymethyl-2,4-(1H,3H,5H)-(1)-benzopyrano-(2,3-d)-pyrimidinedione,
7-methoxymethyl-2,4-(1H,3H,5H)-(1)-benzopyrano-(2,3-d)-pyrimidinedione.

EXAMPLE XII

7-BROMOMETHYL-2,4-(1H,3H,5H)-(1)-BENZOPYRANO-(2,3-d)-PYRIMIDINEDIONE

To ice cold concentrated HBr (48%), (80 ml), add concentrated H₂SO₄ (10 ml) slowly and with continuous cooling. To this solution add 7-hydroxymethyl-2,4-(1H,3H,5H)-(1)-benzopyrano-(2,3-d)-pyrimidinedione ½ H₂O (10 g). With continuous stirring heat the mixture to 70°–75° C. and gradually add an additional 10 ml of concentrated H₂SO₄. After three days pour the mixture into ice water, filter the mixture, wash the product with water and ethanol to yield 7-bromomethyl-2,4-(1H,3H,5H)-(1)-benzopyrano-(2,3-d)-pyrimidinedione.

EXAMPLE XIII

7-FORMYL-2,4-(1H,3H,5H)-(1)-BENZOPYRANO-(2,3-d)-PYRIMIDINEDIONE

Cool to −20° C. a mixture containing 7-hydroxymethyl-2,4-(1H,3H,5H)-(1)-benzopyrano-(2,3-d)-pyrimidinedione ½ H₂O (10 g), dry dimethyl sulfoxide (60 ml) and hexamethylphosphoramide (100 ml) and to the cooled mixture add, in a portion-wise fashion, methanesulfonic anhydride (25 g) with continuous stirring. Allow the mixture to warm slightly for about one hour. Re-cool to −20° C. slowly, and in a portion-wise fashion add triethylamine (45 g). After warming to room temperature pour the product into acidified water. Filter the product, wash with water then isopropanol and finally with ether. Dry the product to yield 7-formyl-2,4-(1H,3H,5H)-(1)-benzopyrano-(2,3-d)-pyrimidinedione.

EXAMPLE XIV

7-(n-BUTYLAMINOCARBONYL)-2,4-(1H,3H,5H)-(1)-BENZOPYRANO-(2,3-d)-PYRIMIDINEDIONE 7-(imidazolylcarbonyl)-2,4-(1H,3H,5H)-(1)-benzopyrano-(2,3-d)-pyrimidinedione (1 g) is suspended in dry dimethylformamide (60 ml) and n-butylamine (1.1 g) is added. The mixture is stirred at room temperature overnight then at 70° C. for 1½ hours. The product is added to dilute HCl and the solid is collected, washed with water, ethanol and ether and dried to yield the desired 7-(n-butylaminocarbonyl)-2,4-(1H,3H,5H)-(1)-benzopyrano-(2,3-d)-pyrimidinedione, dec. 300° C.

EXAMPLE XV

7-(5-TETRAZOLYLAMINOCARBONYL)-2,4-(1H,3H,5H)-(1)-BENZOPYRANO-(2,3-d)-PYRIMIDINEDIONE

To a suspension of 7-carboxyl-2,4-(1H,3H,5H,)-1-benzopyrano-(2,3-d)-pyrimidinedione (2.46 g) in dry dimethylformamide (160 ml) at 75° C., add (all at once), N,N′-carbonyldiimidazole (3.05 g). Heat the resulting mixture at 68°–73° C. for 20 minutes, then add a solution of 5-aminotetrazole (0.80 g) in dry dimethylformamide (11 ml.) at 40° C. Stir the resulting mixture overnight at room temperature and heat at 50° C. for 24 hours. Chill the resulting mixture at 0° C. for one day, filter, triturate with ether (25 ml), triturate with 20% v/v ethanol/ether, filter, wash with ether and vacuum dry at 54° C. for two hours, to yield 7-(5-tetrazolylaminocarbonyl)-2,4-(1H,3H,5H,)-(1)-benzopyrano-(2,3-d)-pyrimidinedione, dec. 310° C.

Also, by the techniques illustrated by this and the previous example there are produced the following compounds:

7-(2-[2-pyridyl]ethylaminocarbonyl)-2,4-(1H,3H,5H)-(1)-benzopyrano-(2,3-d)-pyrimidinedione, dec. 295° C.,
3-methyl-7-(2-[4-pyridyl]ethylaminocarbonyl)-2,4-(1H,3H,5H)-(1)-benzopyrano(2,3-d)-pyrimidinedione,
5-methyl-7(2-[3-pyridyl]ethylaminocarbonyl)-2,4-(1H,3H,5H)-(1)-benzopyrano-(2,3-d)-pyrimidinedione,
8-(3-[2-pyridyl]propylaminocarbonyl)-2,4-(1H,3H,5H)-(1)-benzopyrano-(2,3-d)-pyrimidinedione,
7-(2-pyridylmethylaminocarbonyl)-2,4-(1H,3H,5H)-(1)-benzopyrano-(2,3-d)-pyrimidinedione,
8-(3-pyridylmethylaminocarbonyl)-2,4-(1H,3H,5H)-(1)-benzopyrano-(2,3-d)-pyrimidinedione,
7-(4-pyridylmethylaminocarbonyl)-2,4-(1H,3H,5H)-(1)-benzopyrano-(2,3-d)-pyrimidinedione,
7-(6′-methyl-2-pyridylethylaminocarbonyl)-2,4-(1H,3H,5H)-(1)-benzopyrano-(2,3-d)-pyrimidinedione,
7-(2-hydroxy-2-phenylethylaminocarbonyl)-2,4-(1H,3H,5H)-(1)-benzopyrano-(2,3-d)-pyrimidinedione,
7-[(1′R,2′S)-(1′-hydroxy-1′-phenylprop-2′-yl)aminocarbonyl]-2,4-(1H,3H,5H)-(1)-benzopyrano-(2,3-d)-pyrimidinedione, m.p. 276°–280° C.,
7-(2-hydroxy-2-[2-pyridyl]ethylaminocarbonyl)-2,4-(1H,3H,5H)-(1)-benzopyrano-2,3-d)-pyrimidinedione,
8-(2-hydroxy-2-[2-pyridyl]ethylaminocarbonyl)-2,4-(1H,3H,5H)-(1)-benzopyrano-(2,3-d)-pyrimidinedione,
7-(2-hydroxy-2-phenyl-2-[2-pyridyl]ethylaminocarbonyl)-2,4-(1H,3H,5H)-(1)-benzopyrano-(2,3-d)-pyrimidinedione,
7-(2-hydroxy-2-phenyl-2-[3-pyridyl]ethylaminocarbonyl)-2,4-(1H,3H,5H)-(1)-benzopyrano-(2,3-d)-pyrimidinedione,
7-(2-hydroxy-2-phenyl-2-[6-methyl-2-pyridyl]ethylaminocarbonyl)-2,4-(1H,3H,5H)-(1)-benzopyrano-(2,3-d)-pyrimidinedione,
7-(methoxyethylaminocarbonyl)-2,4-(1H,3H,5H)-(1)-benzopyrano-(2,3-d)-pyrimidinedione, dec. 320° C.
7-(2′-hydroxyethylaminocarbonyl)-2,4-(1H,3H,5H)-(1)-benzopyrano-(2,3-d)-pyrimidinedione, chars 325° C., 7-(3'-hydroxypropylaminocarbonyl)-2,4-(1H,3H,5H)-(1)-benzopyrano-(2,3-d)-pyrimidinedione,
7-(2',2',2'-trifluoroethylaminocarbonyl)-2,4-(1H,3H,5H)-(1)-benzopyrano-(2,3-d)-pyrimidinedione, m.p. >325° C.,
7-(3',3',3'-trifluoropropylaminocarbonyl)-2,4-(1H,3H,5H)-(1)-benzopyrano-(2,3-d)-pyrimidinedione,
7-(2',2',3',3',3'-pentafluoropropylaminocarbonyl)-2,4-(1H,3H,5H)-(1)-benzopyrano-(2,3-d)-pyrimidinedione,
7-(dimethylaminocarbonyl)-2,4-(1H,3H,5H)-(1)-benzopyrano-(2,3-d)-pyrimidinedione,
7-(diethylaminocarbonyl)-2,4-(1H,3H,5H)-(1)-benzopyrano-(2,3-d)-pyrimidinedione,
7-(morpholinocarbonyl)-2,4-(1H,3H,5H)-(1)-benzopyrano-(2,3-d)-pyrimidinedione,
7-(pyrrolidinocarbonyl)-2,4-(1H,3H,5H)-(1)-benzopyrano-(2,3-d)-pyrimidinedione,
7-(piperidinocarbonyl)-2,4-(1H,3H,5H)-benzopyrano-(2,3-d)-pyrimidinedione, m.p. >300° C.,
7-(N'-methylpiperazinylcarbonyl)-2,4-(1H,3H,5H)-(1)-benzopyrano-(2,3-d)-pyrimidinedione,
7-(N'-hydroxyethylpiperazinylcarbonyl)-2,4-(1H,3H,5H)-(1)-benzopyrano-(2,3-d)-pyrimidinedione,
7-(diallylaminocarbonyl)-2,4-(1H,3H,5H)-(1)-benzopyrano-(2,3-d)-pyrimidinedione, dec. 205° C.,
7-(methylthioethylaminocarbonyl)-2,4-(1H,3H,5H)-(1)-benzopyrano-(2,3-d)-pyrimidinedione,
7-(methylsulfoxyethylaminocarbonyl)-2,4-(1H,3H,5H)-(1)-benzopyrano-(2,3-d)-pyrimidinedione,
7-(methylsulfonylethylaminocarbonyl)-2,4-(1H,3H,5H)-(1)-benzopyrano-(2,3-d)-pyrimidinedione,
7-(2-thiazolylaminocarbonyl)-2,4-(1H,3H,5H)-(1)-benzopyrano-(2,3-d)-pyrimidinedione, m.p. >325° C.
7-(2-oxazolylaminocarbonyl)-2,4-(1H,3H,5H)-(1)-benzopyrano-(2,3-d)-pyrimidinedione,
7-(2-(1,3,4-thiadiazolyl)-aminocarbonyl)-2,4-(1H,3H,5H)-(1)-benzopyrano-(2,3-d)-pyrimidinedione,
7-(2-(5-methyl-1,3,4-thiadiazolyl)-2,4-(1H,3H,5H)-(1)-benzopyrano-(2,3-d)-pyrimidinedione,
8-ethylaminocarbonyl-2,4-(1H,3H,5H)-(1)-benzopyrano-(2,3-d)-pyrimidinedione,
8-n-propylaminocarbonyl-2,4-(1H,3H,5H)-(1)-benzopyrano-(2,3-d)-pyrimidinedione,
9-bromo-7-n-butylaminocarbonyl-2,4-(1H,3H,5H)-(1)-benzopyrano-(2,3-d)-pyrimidinedione, chars 300° C.,
8-iso-butylaminocarbonyl-2,4-(1H,3H,5H)-(1)-benzopyrano-(2,3-d)-pyrimidinedione,
8-n-pentylaminocarbonyl-2,4-(1H,3H,5H)-(1)-benzopyrano-(2,3-d)-pyrimidinedione,
7-(5-(1,2,4-thiadiazolyl)aminocarbonyl)-2,4-(1H,3H,5H)-(1)-benzopyrano-(2,3-d)-pyrimidinedione,
7-(5-(3-methyl-1,2,4-thiadiazolyl)-2,4-(1H,3H,5H)-(1)-benzopyrano-(2,3-d)-pyrimidinedione,
7-(2-furylaminocarbonyl)-2,4-(1H,3H,5H)-(1)-benzopyrano-(2,3-d)-pyrimidinedione,
7-(3-pyrazolylaminocarbonyl)-2,4-(1H,3H,5H)-(1)-benzopyrano-(2,3-d)-pyrimidinedione,
7-(2-methyl-5-tetrazolylaminocarbonyl)-2,4-(1H,3H,5H)-(1)-benzopyrano-(2,3-d)-pyrimidinedione,
7-(n-butylaminocarbonyl)-2,4-(1H,3H,5H)-(1)-benzopyrano-(2,3-d)-pyrimidinedione,
7-methylaminocarbonyl-2,4-(1H,3H,5H)-(1)-benzopyrano-(2,3-d)-pyrimidinedione,
7-ethylaminocarbonyl-2,4-(1H,3H,5H)-(1)-benzopyrano-(2,3-d)-pyrimidinedione,
7-n-propylaminocarbonyl-2,4-(1H,3H,5H)-(1)-benzopyrano-(2,3-d)-pyrimidinedione, dec. 278° C.,
7-isopropylaminocarbonyl-2,4-(1H,3H,5H)-(1)-benzopyrano-(2,3-d)-pyrimidinedione,
7-isobutylaminocarbonyl-2,4-(1H,3H,5H)-(1)-benzopyrano-(2,3-d)-pyrimidinedione,
7-sec-butylaminocarbonyl-2,4-(1H,3H,5H)-(1)-benzopyrano-(2,3-d)-pyrimidinedione,
7-tert-butylaminocarbonyl-2,4-(1H,3H,5H)-(1)-benzopyrano-(2,3-d)-pyrimidinedione,
7-n-pentylaminocarbonyl-2,4-(1H,3H,5H)-(1)-benzopyrano-(2,3-d)-pyrimidinedione, chars 300° C.,
7-n-hexylaminocarbonyl-2,4-(1H,3H,5H)-(1)-benzopyrano-(2,3-d)-pyrimidinedione,
7-n-octylaminocarbonyl-2,4-(1H,3H,5H)-(1)-benzopyrano-(2,3-d)-pyrimidinedione,
7-n-decylaminocarbonyl-2,4-(1H,3H,5H)-(1)-benzopyrano-(2,3-d)-pyrimidinedione, m.p. >300° C.,
7-benzylaminocarbonyl-2,4-(1H,3H,5H)-(1)-benzopyrano-(2,3-d)-pyrimidinedione,
7-benzhydryl-aminocarbonyl-2,4-(1H,3H,5H)-(1)-benzopyrano-(2,3-d)-pyrimidinedione,
7-cyclopropylaminocarbonyl-2,4-(1H,3H,5H)-(1)-benzopyrano-(2,3-d)-pyrimidinedione,
7-cyclobutylaminocarbonyl-2,4-(1H,3H,5H)-(1)-benzopyrano-(2,3-d)-pyrimidinedione,
7-cyclopentylaminocarbonyl-2,4-(1H,3H,5H)-(1)-benzopyrano-(2,3-d)-pyrimidinedione,
7-cyclohexylaminocarbonyl-2,4-(1H,3H,5H)-(1)-benzopyrano-(2,3-d)-pyrimidinedione, m.p. >300° C.,
7-cycloheptylaminocarbonyl-2,4-(1H,3H,5H)-(1)-benzopyrano-(2,3-d)-pyrimidinedione,
7-cyclopropylmethylaminocarbonyl-2,4-(1H,3H,5H)-(1)-benzopyrano-(2,3-d)-pyrimidinedione,
7-cyclobutylmethylaminocarbonyl-2,4-(1H,3H,5H)-(1)-benzopyrano-(2,3-d)-pyrimidinedione,
7-(2-[3-pyridyl]ethylaminocarbonyl)-2,4-(1H,3H,5H)-(1)-benzopyrano-(2,3-d)-pyrimidinedione,
7-(2-[4-pyridyl]ethylaminocarbonyl)-2,4-(1H,3H,5H)-(1)-benzopyrano-(2,3-d)-pyrimidinedione,
7-(2-[N-piperidinyl]ethylaminocarbonyl-2,4-(1H,3H,5H)-(1)-benzopyrano-(2,3-d)-pyrimidinedione,
7-(2-[2-pyridyl]propylaminocarbonyl-2,4-(1H,3H,5H)-(1)-benzopyrano-(2,3-d)-pyrimidinedione,
7-(3-[2-pyridyl]-propylaminocarbonyl-2,4-(1H,3H,5H)-(1)-benzopyrano-(2,3-d)-pyrimidinedione,
7-(3-[3-pyridyl]propylaminocarbonyl-2,4-(1H,3H,5H)-(1)-benzopyrano-(2,3-d)-pyrimidinedione,
7-(3-[4-pyridyl]propylaminocarbonyl-2,4-(1H,3H,5H)-(1)-benzopyrano-(2,3-d)-pyrimidinedione,
7-(6-methyl-2-pyridylmethylaminocarbonyl-2,4-(1H,3H,5H)-(1)-benzopyrano-(2,3-d)-pyrimidinedione,
7-(2-phenyl-2-[2-pyridyl]-ethylaminocarbonyl)-2,4-(1H,3H,5H)-(1)-benzopyrano-(2,3-d)-pyrimidinedione,
7-(2-phenyl-2-[3-pyridyl]-ethylaminocarbonyl)-2,4-(1H,3H,5H)-(1)-benzopyrano-(2,3-d)-pyrimidinedione,
7-(2-phenyl-2-[4-pyridyl]-ethylaminocarbonyl)-2,4-(1H,3H,5H)-(1)-benzopyrano-(2,3-d)-pyrimidinedione, 7-(3-phenyl-3-[2-pyridyl]-propylaminocarbonyl)-2,4-(1H,3H,5H)-(1)-benzopyrano-(2,3-d)-pyrimidinedione, 7-(3-phenyl-3-[3-pyridyl]-propylaminocarbonyl)-2,4-(1H,3H,5H)-(1)-benzopyrano-(2,3-d)-pyrimidinedione, 7-(3-phenyl-3-[4-pyridyl]-propylaminocarbonyl)-2,4-(1H,3H,5H)-(1)-benzopyrano-(2,3-d)-pyrimidinedione, 7-(3-phenyl-3-[6-methyl-2-pyridyl]-propylaminocarbonyl)-2,4-(1H,3H,5H)-(1)-benzopyrano-(2,3-d)-pyrimidinedione, 7-(2,2-diphenylethylaminocarbonyl)-2,4-(1H,3H,5H)-(1)-benzopyrano-(2,3-d)-pyrimidinedione, 7-(2-phenylethylaminocarbonyl)-2,4-(1H,3H,5H)-(1)-benzopyrano-(2,3-d)-pyrimidinedione, 7-(2-[2-pyridyl]-ethyl-N-methylaminocarbonyl)-2,4-(1H,3H,5H)-(1)-benzopyrano-(2,3-d)-pyrimidinedione, 2'-[7-(2,4-(1H,3H,5H)-(1)-benzopyrano-(2,3-d)-pyrimidinedionyl) carboxamido]acetamide.

EXAMPLE XVI

7-IMIDAZOLYLCARBONYL-2,4-(1H,3H,5H)-(1)-BENZOPYRANO-(2,3-d)-PYRIMIDINEDIONE

Suspend 7-carboxy-2,4-(1H,3H,5H)-(1)-benzopyrano-(2,3-d)-pyrimidinedione (57 g) in dry dimethylformamide at 40° C. Add carbonyldiimidazole (114 g) in portions, waiting until the reaction subsides before adding the next portion. After all has been added, warm the mixture to 70° C. for 3 hours then allow to stand at room temperature overnight. Filter off the solid. Wash with isopropanol and ether consecutively, and dry to yield 7-imidazolylcarbonyl-2,4-(1H,3H,5H)-(1)-benzopyrano-(2,3-d)-pyrimidinedione. The compounds of this invention (I) have the applied use characteristic of being anti-allergic agents useful in the prophylactic treatment of sensitized animals for allergy and anaphylactic reaction of a reagin or non-reagin mediated nature and as such are useful in the treatment of such disease states as all forms of asthma, allergic rhinitis, and any allergic condition induced by reaginic antibodies.

In testing the compounds of this invention, the two primary assays utilized are the Passive Cutaneous Anaphylaxis (PCA) assay and the Antigen induced histamine release from rat peritoneal mast cells passively sensitized in vivo assay. The compounds are additionally tested as antagonists of intradermally injected histamine and serotonin; these secondary tests show that the compounds are not working as classical antihistamine or antiserotonin anti-allergy agents.

These tests may be briefly described as follows: Preparation of Antisera Containing Homocytotropic Antibody (IgE) to N. Brasiliensis: Male Sprague-Dawley rats, 150–200 g., were injected subcutaneously with 3000 larvae and 28 days later were reinfected with 3000 larvae. Serum was collected 7–12 days following reinfection and frozen in small aliquots at −40° C.

Preparation of Antigen: Adult worms were harvested from the small intestine of rats 8–11 days after infection with larvae. A homogenate was prepared from a suspension of worms in 0.15 M saline using a ground glass homogenizer. The homogenate was centrifuged at 3000×g. for 15 minutes in a Sorvall RC2-B centrifuge. The supernatant was carefully removed and frozen at −40° C. Just prior to use as antigen, the supernatant was adjusted to a concentration of 5 mg. protein per millimeter. All antigen preparations were standardized in this way although it is recognized that the protein concentration of this crude worm extract does not necessarily reflect the amount of specific antigen present in the extract.

Passive Cutaneous Anaphylaxis (PCA): Male Sprague-Dawley rats weighing 250–300 g. were used for PCA reactions. Nine two-fold dilutions of antisera containing homocytotropic antibodies against N. brasiliensis were made in 0.15 M saline. Each dilution was injected intradermally at separate sites onto the shaved backs of normal rats and 48 hours later the animals were challenged intravenously with 0.1 ml. antigen (worm extract) mixed with 0.9 ml. of one percent Evans blue dye. The animals were sacrificed 45 minutes following antigen challenge, skinned, and the area of blueing measured with a millimeter rule. The diameter of the sites of reaction were graded as follows:

| Diameter | Score |
| --- | --- |
| 20 (or greater) | 4 |
| 15–19 | 3 |
| 14–10 | 2 |
| 5–9 | 1 |

The intensity of the reaction was also graded from 0–4.

Histamine Release from Rat Peritoneal Mast Cells Passively Sensitized in vivo: The method used in these studies is a modification of that of Orange, et al. Briefly, male Sprague-Dawley rats (CD strain), 150–200 g were injected i.p. with 2.0 ml. of a dilution of rat antisera containing HA. Two hours later the animals were challenged with 100 mg. worm protein in 5.0 ml. Tyrode's solution containing 50 mg/ml of heparin. Exactly five minutes later, the peritoneal fluid was harvested and centrifuged at 150×g for five minutes at 4° C. The supernatants were removed, and the cells were resuspended in 1.0 ml. Tyrode's and boiled for seven minutes to extract residual cell histamine. The supernatant and cell extracts were frozen at −70° C. and later assayed for their histamine content.

Histamine Release in vitro from Passively Sensitized Mast Cells: Peritoneal mast cells were obtained from normal animals, pooled, washed and resuspended in Tyrode's minus gelatin buffer. An equal volume of serum containing rat homocytotropic antibody was added to the cell suspension and the mixture was incubated at 37° C. for two hours in a metabolic shaker. The suspension was then centrifuged at 150×g for 10 minutes and the supernatant discarded. The cells were resuspended in Tyrode's minus gelatin, combined with antigen, and incubated for five minutes at 37° C. The cells were harvested by centrifugation and the supernatants immediately frozen at −70° C. Residual histamine was extracted from the cells by boiling them for seven minutes in 1.0 ml of Tyrode's minus gelatin.

Histamine Release in vitro from Actively Sensitized Mast Cells: Peritoneal mast cells were obtained from rats 21–28 days following infection with 3000 Nippostrongylus (NB) larvae. The cells were washed and suspended in Tyrode's buffer. Inhibitor dissolved in Tyrode's was added one minute before antigen. An equal volume of antigen, prewarmed to 37° C., was added and the mixture incubated at 37° C. for 15 minutes. The cells and supernatant were then processed as described above for passive sensitization. Both in vitro methods are essentially those described by Wilson, et al.

Histamine Assay: The fluorescent assay of Shore, et al as modified by Technicon for automated determination of histamine was employed.

Determination of Antihistamine and Antiserotonin Activities of Compounds: Normal rats, 200-250 g., were injected i.d. with 10, 20 and 50 mg. of histamine and/or serotonin at separate sites onto their backs 30 or 60 minutes following i/p. or oral administration of drug, respectively. Immediately following the last i.d. injection, the animals received 1 ml. of a one percent solution of Evans blue dye intravenously. Fifteen minutes later they were sacrificed, and the area of blueing measured with a millimeter rule. Each compound was tested for antihistamine or antiserotonin activity in nine animals.

From these tests, as well as by comparison with known antiallergy agents of similar type activity, (i.e., Intal) it has been found that the compounds are effective in the treatment of the above mentioned allergic disease states and that such activity is not a function of the classical antihistamine and antiserotonin characteristics. The compounds are effective for their end-use at varying dose ranges, depending on the method of administration. For example, the more active compounds have an effective interperitoneal administered dose of 0.1-10 MPK, an effective intravenous administered dose of 0.01-10 MPK, and an effective oral dosage of 10-200 MPK. In general, the compounds of this invention, when compared with the clinical effectiveness of Intal-like compounds in aerosol or inhalation preparations are effective at 1-20 mg. per day.

In their use as anti-allergy agents, the compounds of this invention are administered in unit dosage forms, such as tablets, capsules, pills, powders, granules, sterile parenteral solutions or suspensions, eye drops, oral solutions or suspensions, and oil-in-water and water-in-oil emulsions containing suitable quantities of the compounds of this invention (I).

For oral administration, either solid or fluid unit dosage forms can be prepared. For preparing solid compositions such as tablets, the compounds of this invention (I) are mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs and suspensions can be prepared. The water soluble forms can be dissolved in an aqueous vehicle together with sugar, aromatic flavoring agents and preservatives to form a syrup. An elixir is prepared by using an alcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Additionally, a rectal suppository can be employed to deliver the active compound. This dosage form is of particular interest where the mammal cannot be treated conveniently by means of other dosage forms, such as orally or by insufflation, as in the case of young children or debilitated persons. The active compound can be incorporated into any of the known suppository bases by methods known in the art. Examples of such bases include cocoa butter, polyethylene glycols (Carbowaxes), polyethylene sorbitan monostearate, and mixtures of these with other compatible materials to modify the melting point or dissolution rate. These rectal suppositories can weigh from about 1-2.5 g.

For treatment of allergic conditions of the nose, such as rhinitis, compositions adapted for contact with nasal linings are preferred.

Compositions for inhalation are of three basic types: (1) a powder mixture preferably micropulverized with particle size, preferably from about 1 to about 5 microns; (2) an aqueous solution or suspension to be sprayed with a nebulizer; and (3) an aerosol with volatile propellant in a pressurized container.

The powders are quite simply prepared by mixing a compound of the formula with a solid base which is compatible with lung tissue, preferably lactose. The powders are packaged in a device adapted to emit a measured amount of powder when inhaled through the mouth.

Aqueous solutions are prepared by dissolving the compounds of this invention in water and adding salt to provide an isotonic solution and buffering to a pH compatible with inhalation. The solutions are dispersed in a spray device or nebulizer and sprayed into the mouth while inhaling.

Aerosols are prepared by dispersing a compound of the compounds of this invention (I) in water or ethanol, and mixing with a volatile propellant and placing in a pressurized container having a metering valve to release a predetermined amount of material.

The following are specific examples of effective pharmaceutical formulations by which the compounds of this invention may be administered.

FORMULATION I

A lot of 10,000 tablets, each containing 1 mg. of 7-(5-tetrazolylaminocarbonyl)-2,4-(1H,3H,5H)-(1)-benzopyrano-(2,3-d)-pyrimidinedione is prepared from the following types and amounts of ingredients:

| | |
|---|---|
| 7-(5-tetrazolylaminocarbonyl)-2,4- | 10 gm. |

| | |
|---|---|
| (1H,3H,5H)-(1)-benzopyrano-(2,3-d)-pyrimidinedione | |
| Dicalcium phosphate | 1000 gm. |
| Methylcellulose U.S.P. (15 cps) | 60 gm. |
| Talc | 150 gm. |
| Corn starch | 200 gm. |
| Magnesium stearate | 10 gm. |

The compound and dicalcium phosphate are mixed well, granulated with 7.5 percent solution of methylcellulose in water, passed through a No. 8 screen and dried carefully. The dried granules are passed through a No. 12 screen, mixed thoroughly with talc, starch and magnesium stearate, and compressed into tablets.

FORMULATION II

One thousand tablets, each containing 50 mg. of 7-(5-tetrazolylaminocarbonyl)-2,4-(1H,3H,5H)-(1)-benzopyrano-(2,3-d)-pyrimidinedione are preferred from the following types and amounts of ingredients:

| | |
|---|---|
| 7-(5-tetrazolylaminocarbonyl)-2,4-(1H,3H,5H)-(1)-benzopyrano-(2,3-d)-pyrimidinedione | 50 gm. |
| Microcrystalline cellulose, NF | 410 gm. |
| Starch | 100 gm. |
| Magnesium stearate powder | 3 gm. |

The ingredients are screened and blended together and pressed into tablets.

FORMULATION III

A sterile preparation suitable for intrasmuscular injection and containing 0.5 gm. of 7-(5-tetrazolylaminocarbonyl)-2,4-(1H,3H,5H)-(1)-benzopyrano-(2,3-d)-pyrimidinedione in each milliliter is prepared from the following ingredients:

| | |
|---|---|
| 7-(5-tetrazolylaminocarbonyl)-2,4-(1H,3H,5H)-(1)-benzopyrano-(2,3-d)-pyrimidinedione | 0.5 gm. |
| Benzyl benzoate | 200 gm. |
| Methylparaben | 1.5 gm. |
| Propylparaben | 0.5 gm. |
| Cottonseed oil q.s. | 1000 gm. |

FORMULATION IV

Six hundred ml. of an aqueous suspension containing 5.0 mg. of the 7-(5-tetrazolylaminocarbonyl)-2,4-(1H,3H,5H)-(1)-benzopyrano-(2,3-d)-pyrimidinedione per ml. is prepared as follows:

| | |
|---|---|
| 7-(5-tetrazolylaminocarbonyl)-2,4-(1H,3H,5H)-(1)-benzopyrano-(2,3-d)-pyrimidinedione | 3.0 gm. |
| Sodium chloride | 5.0 gm. |
| Water for injection q.s. | 600 ml. |

The 7-(5-tetrazolylaminocarbonyl)-2,4-(1H,3H,5H)-(1)-benzopyrano-(2,3-d)-pyrimidinedione and sodium chloride are dispersed in sufficient water to make 600 ml. and sterilized. The liquid is placed in nebulizers designed to deliver 0.25 ml. per spray.

FORMULATION V

A powder mixture consisting of 0.1 g of 7-(5-tetrazolylaminocarbonyl)-2,4-(1H,3H,5H)-(1)-benzopyrano-(2,3-d)-pyrimidinedione and sufficient lactose to make 5 g. of mixture is micropulverized and placed in an insufflator designed to deliver 50 mg. of powder per dose.

The powder is inhaled into the lungs every 4 to 6 hours for prevention of asthmatic attacks.

The powder is inhaled intranasally every 4 hours for prevention of rhinitis.

FORMULATION VI

One thousand tablets, each containing 5 mg. of 7-[2-(2-pyridyl)ethylaminocarbonyl]-2,4-(1H,3H,5H)-(1)-benzopyrano-(2,3-d)-pyrimidinedione hydrochloride are prepared from the following types and amounts of ingredients:

| | |
|---|---|
| 7-[2-(2-pyridyl)ethylaminocarbonyl]-2,4-(1H,3H,5H)-(1)-benzopyrano-(2,3-d)-pyrimidinedione hydrochloride | 5 gm. |
| Microcrystalline cellulose NF | 410 gm. |
| Stach | 100 gm. |
| Magnesium stearate powder | 3 gm. |

The ingredients are screened and blended together and pressed into tablets.

As is true for most generic classes of compounds suitable for use as therapeutic agents, certain subgeneric and certain specific agents have a better biological profile than others. In this particular instance, those compounds having a carboxamido radical at the 7- or 8-positions, or a acyloxyalkyl radical at the 7- or 8-positions, or an alkoxycarbonyl radical at the 7- or 8-positions are most preferred. Preferably the 3- and/or the 5-positions are unsubstituted, but methyl radicals at one or the other position when "A" represents a carboxamido, acyloxyalkyl or alkoxycarbonyl radical are advantageously employed. Specifically, desirable compounds are:

7-isopropyloxycarbonyl-2,4-(1H,3H,5H)-(1)-benzopyrano-(2,3-d)-pyrimidinedione,
7-(n-butyryloxymethyl)-2,4-(1H,3H,5H)-(1)-benzopyrano-(2,3-d)-pyrimidinedione,
7-(isobutyryloxymethyl)-2,4-(1H,3H,5H)-(1)-benzopyrano-(2,3-d)-pyrimidinedione,
7-(isovaleryloxymethyl)-2,4-(1H,3H,5H)-(1)-benzopyrano-(2,3-d)-pyrimidinedione,
7-(n-propylaminocarbonyl)-2,4-(1H,3H,5H)-(1)-benzopyrano-(2,3-d)-pyrimidinedione,
7-(isopropylaminocarbonyl)-2,4-(1H,3H,5H)-(1)-benzopyrano-(2,3-d)-pyrimidinedione,
7-(n-butylaminocarbonyl)-2,4-(1H,3H,5H)-(1)-benzopyrano-(2,3-d)-pyrimidinedione,
7-(isobutylaminocarbonyl)-2,4-(1H,3H,5H)-(1)-benzopyrano-(2,3-d)-pyrimidinedione,
7-(2-hydroxyethylaminocarbonyl)-2,4-(1H,3H,5H)-(1)-benzopyrano-(2,3-d)-pyrimidinedione,
7-(tris-hydroxymethyl-methylaminocarbonyl)-2,4-(1H,3H,5H)-(1)-benzopyrano-(2,3-d)-pyrimidinedione,
7-(2-hydroxy-2-phenylethylaminocarbonyl)-2,4-(1H,3H,5H)-(1)-benzopyrano-(2,3-d)-pyrimidinedione,
7-(2-(2-pyridyl)ethylaminocarbonyl)-2,4-(1H,3H,5H)-(1)-benzopyrano-(2,3-d)-pyrimidinedione,
7-(2-pyridylmethylaminocarbonyl-2,4-(1H,3H,5H)-(1)-benzopyrano-(2,3-d)-pyrimidinedione, 7-(3-(2-pyridyl)-propylaminocarbonyl)-2,4-(1H,3H,5H)-(1)-benzopyrano-(2,3-d)-pyrimidinedione, 3-methyl-7-(5-tetrazolylaminocarbonyl)-2,4-(1H,3H,5H)-(1)-benzopyrano-(2,3-d)-pyrimidinedione, 3-methyl-7-(2-[2-pyridyl]ethylaminocarbonyl)-2,4-(1H,3H,5H)-(1)-benzopyrano-(2,3-d)-pyrimidinedione, and 7-(5-tetrazolyl)carbamyl-2,4-(1H,3H,5H)-benzo-(1)-pyrano-[2,3-d]-pyrimidinedione.

I claim:

1. A compound of the formula

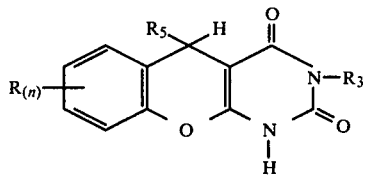

wherein each of $R_3$ and $R_5$ is hydrogen or loweralkyl, n is an integer from one to four and R is hydrogen, loweralkyl, lowercycloalkyl, acyloxyloweralkyl, hydroxyloweralkyl, loweralkoxyloweralkyl, nitro, halogeno, haloloweralkyl, hydroxy, loweralkoxy, acylaminoloweralkyl, mono- or diloweralkylaminoloweralkyl, alkanoyloxy, carboxy, loweralkoxycarbonyl, acyl, formyl, cyano or a carboxamido moiety of the structure

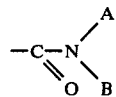

wherein A is straight or branched chain alkyl with up to 12 carbon atoms, lowercycloalkyl, lowercycloalkylloweralkyl, loweralkoxyloweralkyl, hydroxyloweralkyl, fluoroloweralkyl, loweralkenyl, loweralkylthioloweralkyl, loweralkylsulfoxyloweralkyl, loweralkylsulfonylloweralkyl, thiazolyl, oxazolyl, thiadiazolyl, methylthiadiazolyl, furyl, pyrazolyl, tetrazolyl, methyltetrazolyl, or the grouping $$-E-\overset{O}{\underset{\|}{C}}-Q$$

wherein E is a straight or branched chain or cyclic loweralkylene, and Q is hydroxy, loweralkoxy, amino or mono- or diloweralkylamino; or the grouping —E—$R_8$, wherein E is as defined above or E is as defined above and E is substituted by hydroxy, by phenyl, or by both hydroxy and phenyl, $R_8$ is phenyl, thiazolyl, oxazolyl, thiadiazolyl, methylthiadiazolyl, tetrazolyl, methyltetrazolyl, furyl, pyridyl, methylpyridyl or piperidinyl; and B is hydrogen, loweralkyl; lowercycloalkyl, lowercycloalkylloweralkyl, or loweralkenyl; or A and B, when taken together with the nitrogen atom to which they are attached, represent imidazolyl, morpholinyl, pyrrolidinyl, piperidinyl or piperazinyl said heterocyclic rings being optionally substituted by hydroxy, loweralkyl or hydroxyloweralkyl; and pharmaceutically acceptable salts thereof.

2. A compound according to claim 1, wherein each of $R_3$ and $R_5$ are hydrogen or loweralkyl, n is an integer from one to four and R is hydrogen, loweralkyl, lowercycloalkylloweralkyl, acyloxyloweralkyl, hydroxyloweralkyl, loweralkoxyloweralkyl, nitro, halogeno, haloloweralkyl, hydroxy, loweralkoxy, acylaminoloweralkyl, mono- or diloweralkylaminoloweralkyl, alkanoyloxy, carboxy, loweralkoxycarbonyl, acyl, formyl, cyano or a carboxamido moiety of the structure

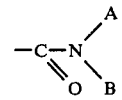

wherein A is straight or branched chain alkyl with up to 12 carbon atoms, lowercycloalkylloweralkyl, loweralkoxyloweralkyl, hydroxyloweralkyl, fluoroloweralkyl, loweralkenyl, loweralkylthioloweralkyl, thiazolyl, thiadiazolyl, methylthiadiazolyl, tetrazolyl, methyltetrazolyl, or the grouping —E—$R_8$, where E is a straight or branched chain loweralkylene or E is a straight or branched chain loweralkylene substituted by hydroxy, by phenyl, or by both hydroxy and phenyl, $R_8$ is phenyl, tetrazolyl, methyltetrazolyl, pyridyl, methylpyridyl or piperidinyl; and B is hydrogen, loweralkyl, or loweralkenyl; or A and B, when taken together with the nitrogen atom to which they are attached, represent imidazolyl, morpholinyl, pyrrolidinyl, piperidinyl or piperazinyl, and pharmaceutically acceptable salts thereof.

3. A compound according to claim 1, wherein $R_3$ and $R_5$ are hydrogen.

4. A compound according to claim 1, wherein n is one.

5. A compound according to claim 1, wherein n is two.

6. A compound according to claim 1, wherein R is located in at least one of positions 7 and 8.

7. A compound according to claim 6, wherein R is selected from halogeno, carboxy, loweralkoxycarbonyl, acylaminoloweralkyl, acyloxyloweralkyl and carboxamido moiety as defined in claim 1.

8. A compound according to claim 1, wherein R is located in position 7 or 8 and is selected from loweralkoxycarbonyl, acyloxyloweralkyl and the carboxamido moiety as defined in claim 11.

9. A compound according to claim 1, wherein, in the carboxamido moiety of the structure as defined in claim 1, A is straight or branched chain alkyl with up to 12 carbon atoms, hydroxyloweralkyl, tetrazolyl or the grouping —E—$R_8$, wherein E is a straight chain alkylene with up to three carbon atoms or E is straight chain alkylene with up to three carbon atoms that is substituted by hydroxy, and $R_8$ is phenyl, tetrazolyl or pyridyl; and B is hydrogen or loweralkyl.

10. A compound according to claim 1, wherein, in the carboxamido moiety of the structure as defined in claim 1, A is tetrazolyl or the grouping —E—$R_8$, wherein E is methylene or ethylene and $R_8$ is phenyl or pyridyl; and B is hydrogen; the carboxamido moiety being in position 7.

11. A compound according to claim 1, namely 7-(5-tetrazolylaminocarbonyl)-2,4-(1H,3H,5H)-(1)-benzopyrano-(2,3-d)-pyrimidinedione.

12. A compound according to claim 1, namely 7-(2-[2-pyridyl]ethylaminocarbonyl)-2,4-(1H,3H,5H)-(1)-benzopyrano-(2,3-d)-pyrimidinedione.

13. A compound according to claim 1, wherein $R_3$ and $R_5$ are hydrogen, n is one and R is halogeno.

14. A compound according to claim 1, wherein $R_3$ and $R_5$ are hydrogen, n is one and R is carboxy.

15. A compound according to claim 1, wherein $R_3$ and $R_5$ are hydrogen, n is one and R is loweralkoxycarbonyl.

16. A compound according to claim 1, wherein $R_3$ and $R_5$ are hydrogen, n is one and R is acylaminoloweralkyl.

17. A compound according to claim 1, wherein $R_3$ and $R_5$ are hydrogen, n is one and R is acyloxyloweralkyl.

18. A compound according to claim 1, wherein $R_3$ and $R_5$ are hydrogen, n is one and R is carboxamido moiety as defined in claim 1.

19. A compound according to claim 18, wherein the carboxamido moiety is located at the 7-position.

20. A compound according to claim 18, wherein the carboxamido moiety is located at the 8-position.

21. A method for effecting an anti-allergic reaction which comprises administering an effective amount of a compound as claimed in claim 1 to an animal.

22. An anti-allergic pharmaceutical composition containing as active ingredient an effective amount of at least one compound as claimed in claim 1 together with a pharmaceutical carrier or excipient.

* * * * *